United States Patent [19]

Herrman et al.

[11] Patent Number: 5,274,183

[45] Date of Patent: Dec. 28, 1993

[54] WATER-SOLUBLE SULFONATED DIPHOSPHINES

[75] Inventors: Wolfgang Herrman, Freising; Christian Kohlpaintner, Stephanskirchen; Helmut Bahrmann, Hamminkelm, all of Fed. Rep. of Germany

[73] Assignee: Hoechst Aktiengesellschaft, Fed. Rep. of Germany

[21] Appl. No.: 950,421

[22] Filed: Sep. 23, 1992

Related U.S. Application Data

[62] Division of Ser. No. 807,977, Dec. 16, 1991, abandoned.

[30] Foreign Application Priority Data

Dec. 17, 1990 [DE] Fed. Rep. of Germany ....... 4040314

[51] Int. Cl.$^5$ ................................................ C07F 9/50
[52] U.S. Cl. .................................................... 562/35
[58] Field of Search ......................................... 562/35

[56] References Cited

U.S. PATENT DOCUMENTS

| | | | |
|---|---|---|---|
| 4,483,801 | 11/1984 | Sabot | 562/35 |
| 4,483,802 | 11/1984 | Gärtner et al. | 562/35 |
| 4,623,490 | 11/1986 | Bexten et al. | 562/35 |
| 5,171,892 | 12/1992 | Burk | 562/35 |

*Primary Examiner*—Marianne M. Cintins
*Assistant Examiner*—Rebecca Cook
*Attorney, Agent, or Firm*—Jordan B. Bierman

[57] ABSTRACT

The preparation of water-soluble diphosphines derived from biaryl compounds by reaction with a solution of $SO_3$ in sulfuric acid.

12 Claims, No Drawings

WATER-SOLUBLE SULFONATED DIPHOSPHINES

This application is a division of application Ser. No. 07/807977, filed Dec. 16, 1991 now abandoned.

This Application claims the benefit of Application P 40 40 314.9, filed Dec. 17, 1990.

The invention relates to the preparation of diphosphines which are derived from biaryl compounds and are soluble in water as a result of the presence of sulfonic acid radicals in the molecule.

BACKGROUND OF THE INVENTION

Complex compounds which contain, as the central atom, a metal of Group VIII of the Periodic Table of the Elements (IUPAC Version) and, as ligands, P(III) compounds such as phosphines and phosphites, as well as optionally other groups suited for complex formation, have recently become increasingly important as catalysts. Thus, the reaction of olefins with synthesis gas to give aldehydes (hydroformylation), practiced industrially on a large scale, is carried out in the presence of catalyst systems which are composed of cobalt and, in particular, rhodium, and triphenylphosphine. Catalysts based on complex compounds containing phosphines have also proved suitable for the reaction of methanol with synthesis gas to give higher alcohols, in particular ethanol and propanol (homologization). In accordance with the solubility of these catalysts in organic media, the reactions are carried out in the homogeneous phase.

Instead of in the homogeneous phase, the reaction can also be carried out in heterogeneous reaction systems. The advantage of this process variant is the simple and gentle separation of the catalyst, which is dissolved in water, from the water-insoluble reaction product. For example, the process described in DE 27 00 904 C2 for the addition of hydrogen cyanide to an unsaturated organic compound having at least one ethylenic double bond works according to this principle. Suitable catalysts for this reaction are the systems nickel/TPPTS [TPPTS is tri(sulfophenyl)phosphine], palladium/TPPTS, or iron/TPPTS. For the preparation of aldehydes by reaction of olefins with carbon monoxide and hydrogen, according to the process of DE 26 27 354 C2, rhodium is employed as metal or in the form of one of its compounds, together with a water-soluble phosphine, for example TPPTS, as the catalyst.

Diphosphines, which as bidentate ligands are able to form chelates with metal ions, are used only rarely, in contrast to the monophosphines, and then exclusively as constituents of homogeneously dissolved catalysts. Thus, according to the teaching of DE 29 04 782 C2, aldehydes are obtained by hydroformylation of a lower olefinic compound in an organic solvent in the presence of a rhodium complex, a trisubstituted monophosphine, and a diphosphinoalkane.

DE 29 09 041 A1 describes a process for the preparation of aldehydes by hydroformylation of olefins in which platinum is present as the catalyst, the halide of at least one metal of Group IVB of the Periodic Table ("carbon group") is present as the auxiliary catalyst. A two-bonded ligand of the formula $R_2X$-$Z$-$Y$-$Z$-$XR'_2$ (R and R' are each an alkyl, aryl, or aralkyl group; X is phosphorus, arsenic, or antimony; Y is alkylene, arylene, or aralkylene; and Z is methylene or oxygen) is present as the reaction promoter. 2,2'-Bis(diphenylphosphinomethyl)-1,1'-binaphthyl is used in combination with a rhodium or nickel compound as a ligand for asymmetric hydrogenation catalysts according to Laid-open Japanese Patent Application 79/39,059.

A reason for the comparatively rare use of diphosphines as a constituent of catalysts may be the difficulties which stand in the way of their preparation on an industrial scale. A number of laboratory processes for obtaining diphosphines are indeed known, bu their application to industrial production processes is not without problems, both technical and economic.

A process which, inter alia, relates to the preparation of diphosphines - they are used as bidentate phosphorus ligands - is the subject of EP 326,286 A1. Biaryl compounds are employed as starting substances which are substituted in each of the two aryl groups by the radical —$CH(R_3)(R_4)$ and optionally by other radicals. They are converted by the action of proton-eliminating reagents into biaryldianions, which are reacted with phosphorus compounds of the formula X—$P(R_1)(R_2)$ or X—$PO(R_1)(R_2)$, X being preferably a halogen atom. In this manner, diphosphines are obtained directly or, if the phosphorus compound X—$PO(R_1)(R_2)$ was employed, after reduction.

The process described above is suitable only for the preparation of diphosphines which are not substituted or contain substituents which are inert to compounds having reducing action. In this connection, it must be recognized that a reduction step is not only necessary when using reactants of the type X—$P(O)(R_1)(R_2)$. The formation of the biaryldianion also takes place under reducing conditions, as the reagents employed for eliminating the proton, (such as alkali metal hydrides or alkali metal alkyls) have a reducing action. A direct preparation of biarylphosphines containing sulfonic acid groups is, therefore, not possible by the methods described above, because the sulfonic acid groups are not retained in the reaction of the biaryl and phosphorus compounds.

Therefore, the object was to develop a process for the preparation of sulfonated diphosphines which not only solves the problems described, but is also simple to carry out industrially and, moreover, is economical.

SUMMARY OF THE INVENTION

The object described above is achieved by a process for the preparation of water-soluble diphosphines. It comprises treating biaryl compounds of Formula I

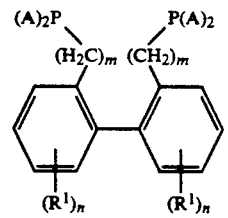

in which the A's are individually alkyl, cycloalkyl, phenyl, tolyl or naphthyl, the $R^1$'s are individually hydrogen, or alkyl or alkoxy radicals having 1 to 14 carbon atoms, cycloalkyl, aryl, or aryloxy radicals having 6 to 14 carbon atoms, or a fused benzene ring, the m's are individually integers from 0 to 5 and the n's are individually integers from 0 to 4, with a solution of sulfur trioxide in sulfuric acid at temperatures of 0° C. to 60° C. The mixture is then allowed to react with vigorous stirring at 20° C. to 60° C. in particular 20° C. to 30° C., over a period of 1 to 60 hours. The reaction mixture is diluted with water while the temperature is maintained at 0° C. to 20° C., in particular 0° C. to 10° C.

Surprisingly, it is possible by the process of the invention to sulfonate biaryls substituted by diorganoalkylenephosphine groups under mild conditions. The term "organo" represents alkyl, cycloalkyl, phenyl, tolyl, or naphthyl. It is particularly remarkable that the formation of oxidation products such as phosphine oxides is largely suppressed. The progress of the sulfonation can be monitored and checked in a simple manner by $^{31}$P-NMR spectroscopy.

DETAILED DESCRIPTION OF THE INVENTION

The biaryls employed as starting compounds in each case contain a —$(CH_2)(A)_2$— radical in the 2- and 2'-positions. A is preferably phenyl, tolyl, or naphthyl. The biaryl molecule can be substituted by one or more radicals $R^1$ which may be the same or different. $R^1$ is, in particular, hydrogen, methyl, isopropyl, isobutyl, t-butyl, phenyl, naphthyl, or a fused benzene ring, m is preferably 1 and n is 0 or 1.

Sulfonated biaryl derivatives which are substituted in the 6-and 6'-position by $R^1$ radicals (when $R^1$ is not a fused benzene ring) are of particular significance. Their presence prevents rotation of the two substituted phenyl radicals. Complex compounds which contain molecules of this type as ligands can therefore be employed as catalysts for enantioselective reactions. For the preparation of the biaryl derivatives containing phosphorus, the biaryls on which they are based are advantageously used as starting materials.

The biaryls are obtained according to prior art processes, for example by coupling aryl Grignard reagents with aryl chloride, bromide, or iodide in the presence of nickel catalysts. Another method is the dehalogenation of aryl bromides and iodides in the presence of powdered active nickel oxides.

For the introduction of the phosphine radical into the biaryl and thus for the preparation of the intermediate for obtaining the sulfonated compound, a novel procedure which starts from easily available starting substances has proved very suitable. It comprises the reaction of 2,2'dilithiobiphenyl or its derivatives of the formula

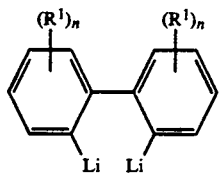

with a diarylphosphine halide of the formula $(A)_2P(CH_2)_mX$, wherein X is halogen preferably chlorine, bromine or iodine. The two reactants are suspended in stoichiometric amounts or with a small excess of one of the two components in an inert organic solvent and the mixture is stirred at temperatures of from —50° C. to 100° C., preferably —20° C. to 50° C. An aliphatic hydrocarbon or a hydrocarbon mixture such as hexane or light petroleum in an aromatic hydrocarbon such as toluene or an ether such as tetrahydrofuran are particularly suitable. The reaction product dissolved in the organic medium is hydrolyzed with water. The diphosphine can be obtained in high yields from the organic phase after removal of the solvent by distillation and an optional purification step.

The diphosphine can be employed for the sulfonation without prior purification. The sulfonating agent used according to the invention is oleum, i.e. a solution of $SO_3$ in sulfuric acid. It is advantageous to employ oleum having an $SO_3$ concentration of 20% to 65% by weight, relative to the solution. An essential feature of the novel procedure is the maintenance of specific reaction temperatures. These are 0° to 60° C., and low temperatures in the range from 0° C. to 20° C. are preferred. In order to ensure that the temperature ranges mentioned are not exceeded, it is recommended that the diphosphine is first dissolved in concentrated sulfuric acid and the solution is then treated with oleum in portions with stirring and intensive cooling. It is then allowed to react with vigorous stirring at 20° C. to 60° C., in particular 20° C. to 30° C., over a period of 1 to 60 hours. $SO_3$ concentrations in the oleum and the period of stirring determine the degree of sulfonation of the diphosphine. The greater the supply of $SO_3$ and the longer the mixture is stirred, the more sulfonic acid groups enter the diphosphine molecule.

As soon as the reaction is complete, the reaction mixture is diluted with water. There are several processes available for this. According to an approved procedure, the sulfuric acid solution is first neutralized. Both during dilution of the reaction mixture and during neutralization, care is to be taken that overheating does not occur and it has proved suitable to maintain temperatures of 0° C. to 20° C., in particular 0° C. to 10° C. The aqueous solution of an alkali metal hydroxide, preferably sodium hydroxide, is used for neutralization. Alkali metal hydroxide concentrations of 20% to 60% by weight, based on the solution, have proven suitable.

In order to achieve precipitation which is as complete as possible of the alkali metal sulfate formed from the sulfuric acid and alkali metal hydroxide, it is recommended to operate at not too great a dilution. Alkali metal sulfate precipitates from the neutralized reaction mixture. It is filtered off and washed several times with a lower alcohol, preferably a $C_1$- to $C_4$- alcohol, in particular methanol. The sulfonated diphosphine is obtained from the filtrate by removal of the solvent under mild conditions, for example by distillation under vacuum produced by an oil pump. For purification, the crystalline product obtained is dissolved in a little water, the solution is mixed with a lower alcohol, preferably a $C_1$- to $C_4$- alcohol, in particular methanol, and filtered, and the solvent is again removed gently.

According to another process (the subject of European Patent 107,006) the acidic aqueous solution of the sulfonation product is extracted with a solution of a water-insoluble amine in a water-insoluble organic solvent. The organic phase is removed and brought into intimate contact with an aqueous solution of a base. The sulfonated diphosphine can then be isolated from the aqueous phase formed.

The sulfonated diphosphines are colorless to yellowish-colored powders. Depending on the sulfonation conditions, they contain 4 to 6 sulfonic acid groups. They dissolve very easily in water and their solubility is 0.5 to 1.5 kg of sulfonation product/liter of water, according to the degree of sulfonation. The free acids and also the salts of other metals can be prepared from the alkali metal salts, for example by ion exchange.

The novel process is illustrated in the subsequent example, but it is not restricted to the embodiments described.

EXAMPLE

1. Preparation of 2,2'-bis(diphenylphosphinomethyl)-biphenyl ("BISBI")

2.34 g (10 mmol) of $ClCH_2PPh_2$, obtained according to Langhans et at., Chem. Ber. 123 (1990), 995-999, is suspended in 30 ml of hexane in a 250 ml three-necked flask provided with a reflux condenser, dropping funnel, and magnetic stirrer. It is treated dropwise with vigorous stirring with a suspension of 0.83 g (5 mmol) of 2,2'-dilithiobiphenyl, obtained according to J. Organomet. Chem. 228 (1982), 107-118, in 30 ml of hexane. The mixture is then maintained at 60° C. for about 30 min and the solution is cooled by addition of 20 ml of toluene. After stirring for 20 minutes, it is carefully hydrolyzed with 10 ml of water. The organic phase is removed in a separating funnel, washed three times with 5 ml portions of water and freed of solvent in an oil pump vacuum at a maximum of 30° C. BISBI is precipitated from the residual viscous oil as a white solid by addition of 15 ml of ethanol and filtered off through a G3 glass frit.

Yield: 70% of theoretical. The batch size can be increased 100-fold without disadvantages or losses yield if reaction vessels and reaction times are increased.

2. Sulfonation of BISBI 1 mmol of BISBI is dissolved in 2 ml of concentrated sulfuric acid and treated dropwise at 0° C. with 5 ml of oleum ($SO_3$ content: 20% to 65% by weight, based on the solution). After warming to room temperature (about 20° C.), the reaction mixture is stirred vigorously for several hours, then poured cautiously onto about 100 g of ice and neutralized at temperature below 5° C. using 50% by weight aqueous NaOH solution. The resulting suspension is filtered and the filtrate is added to 25 ml of methanol. The filter cake is washed twice with 25 ml portions of methanol. The combined fractions are concentrated to dryness in an oil pump vacuum and the residue is dissolved in a very small amount of water. The clear, amber-colored solution is introduced into 30 ml of methanol, the resulting suspension is stirred and filtered, and the filtrate is concentrated to dryness in an oil pump vacuum. The sulfonation period depends on the progress of the reaction, which is monitored by $^{31}P$-nuclear magnetic resonance spectroscopy at intervals of about 2 hours.

Characterization of the reaction product

The reaction product described below was obtained from BISBI, after reaction for 17 hours with 65% oleum.

$^{31}P$-NMR (161.8 MHz, $CD_2Cl_2$, 20° C.): $\delta = -6.8$ (s), $-7.1$ (s), $-9.5$ (s), $-9.6$ (s)

IR (KBr, $cm^{-1}$) $\nu = 993$ (m), 1040 (st), 1098 (m), 1127 (m), 1146 (m), 1195 (sst)

P/S ratio = 2 : 5.7 (elemental analysis)

Solubility: greater than 1 g/ml of water

Appearance: yellowish powder

While only a limited number of specific embodiments of the present invention have been expressly disclosed, it is, nonetheless, to be broadly construed, and not to be limited except by the character of the claims appended hereto.

What we claim is:

1. A water-soluble diphosphine prepared by a process comprising reacting a biaryl compound of the formula

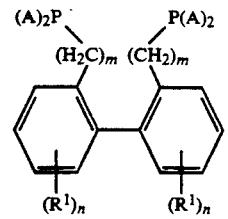

in which the A's are individually alkyl, cycloalkyl, phenyl, tolyl, or naphthyl, the $R^1$'s are individually hydrogen, or alkyl or alkoxy radicals having 1 to 14 carbon atoms, cycloalkyl, aryl, or aryloxy radicals having 6 to 14 carbon atoms, or a fused benzene ring, the m's are individually integers from 0 to 5 and the n's are individually integers from 0 to 4; at initial temperatures of 0° C. to 60° C., with oleum, to form an initial mixture, allowing said initial mixture to subsequently react with vigorous stirring at a reaction temperature of 20° C. to 60° C. over a period of 1 to 60 hours to form a reaction mixture, diluting said reaction mixture with water while maintaining a dilution temperature of from 0° C. to 20° C. to form a dilution mixture.

2. The diphosphine of claim 1 wherein said dilution temperature is 0° C. to 10° C.

3. The diphosphine of claim 1 wherein said oleum contains 20% to 65% by weight of said $SO_3$ based on said oleum.

4. The diphosphine of claim 1 wherein the diluted mixture is further subjected to neutralizing with an aqueous alkali metal hydroxide solution at a neutralizing temperature of 0° C. to 20° C. to yield a precipitated alkali metal sulfate, filtering out said precipitated sulfate from said aqueous solution, concentrating said aqueous solution under mild conditions to form a crystalline product, dissolving said crystalline product in a small amount of water to form a product solution, mixing said product solution with a lower alcohol to form a final solution, filtering said final solution to form a filtrate, and removing said alcohol under mild conditions.

5. The diphosphine of claim 4 wherein said neutralizing temperature is 0° C. to 10° C.

6. The diphosphine of claim 4 wherein said lower alcohol has 1 to 4 carbon atoms.

7. The diphosphine of claim 6 wherein said lower alcohol is methanol.

8. The diphosphine of claim 4 wherein said concentrating comprises vacuum distillation.

9. The diphosphine of claim 4 wherein said removing comprises vacuum distillation.

10. The diphosphine of claim 2 wherein said diluted mixture is extracted with an amine solution of a water-insoluble amine in a water-insoluble organic solvent to form an organic phase, said organic phase being separated and brought into intimate contact with an aqueous base solution to form an aqueous phase and an organic phase, said diphosphine being isolated from said aqueous phase.

11. The diphosphine of claim 1 wherein said reaction temperature is 20° C. to 30° C.

12. The diphosphine of claim 2 wherein said biaryl compound is a product of the reaction of a compound of the formula

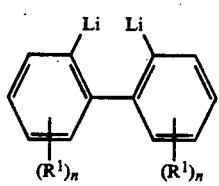

with a halogenated diarylalkylenephosphine of the formula $X(CH_2)_m P(A)_2$ wherein X is chlorine, bromine, or iodine, A is alkyl, cycloalkyl, phenyl, tolyl, or naphthyl, $R^1$'s are individually hydrogen, alkyl or alkoxy radicals having 1 to 14 carbon atoms, cycloalkyl, aryl, or aryloxy radicals having 6 to 14 carbons atoms, or a fused benzene ring, m is an integer from 0 to 5 and n's are individually integers from 0 to 4.

* * * * *